(12) United States Patent
Tashiro

(10) Patent No.: US 12,003,891 B2
(45) Date of Patent: Jun. 4, 2024

(54) IMAGE RECORDING APPARATUS, IMAGE RECORDING METHOD, AND ENDOSCOPE SYSTEM

(71) Applicant: OLYMPUS CORPORATION, Tokyo (JP)

(72) Inventor: Junichi Tashiro, Higashimurayama (JP)

(73) Assignee: OLYMPUS CORPORATION, Tokyo (JP)

(*) Notice: Subject to any disclaimer, the term of this patent is extended or adjusted under 35 U.S.C. 154(b) by 332 days.

(21) Appl. No.: 17/342,667

(22) Filed: Jun. 9, 2021

(65) Prior Publication Data

US 2021/0298584 A1      Sep. 30, 2021

Related U.S. Application Data

(63) Continuation of application No. PCT/JP2018/045286, filed on Dec. 10, 2018.

(51) Int. Cl.
| | |
|---|---|
| A61B 1/00 | (2006.01) |
| A61B 1/04 | (2006.01) |
| A61B 1/045 | (2006.01) |
| H04N 5/77 | (2006.01) |
| H04N 7/18 | (2006.01) |

(52) U.S. Cl.
CPC .......... *H04N 7/18* (2013.01); *A61B 1/00009* (2013.01); *A61B 1/0005* (2013.01); *A61B 1/043* (2013.01); *A61B 1/045* (2013.01); *H04N 5/77* (2013.01); *H04N 7/188* (2013.01)

(58) Field of Classification Search
CPC . H04N 7/18; H04N 5/77; H04N 7/188; A61B 1/00009; A61B 1/0005; A61B 1/043; A61B 1/045

USPC .......................................................... 348/71
See application file for complete search history.

(56) References Cited

U.S. PATENT DOCUMENTS

| | | | |
|---|---|---|---|
| 2004/0030367 A1 | 2/2004 | Yamaki et al. | |
| 2006/0173240 A1 | 8/2006 | Fukuyama et al. | |
| 2016/0296107 A1* | 10/2016 | Kubo ................... | A61K 49/006 |

(Continued)

FOREIGN PATENT DOCUMENTS

| | | | |
|---|---|---|---|
| CN | 109152584 B * | 3/2022 | ......... A61B 1/00009 |
| EP | 3081144 A1 | 10/2016 | |
| JP | H07-171115 A | 7/1995 | |

(Continued)

OTHER PUBLICATIONS

International Search Report dated Jan. 15, 2019 issued in PCT/JP2018/045286.

*Primary Examiner* — John W Miller
*Assistant Examiner* — Omer Khalid
(74) *Attorney, Agent, or Firm* — Scully, Scott, Murphy & Presser, P.C.

(57) ABSTRACT

An image recording apparatus includes a processor. The processor records setting information corresponding to at least one of a procedure or a scene during the procedure, sets a color to be detected from a fluorescent image and a detection level based on the setting information, detects a level of the set color from the fluorescent image inputted, and outputs signals to start and stop recording of the inputted fluorescent image by comparing the detected level of the color with a threshold based on the detection level.

10 Claims, 10 Drawing Sheets

(56) References Cited

U.S. PATENT DOCUMENTS

2018/0220873 A1   8/2018   Tani

FOREIGN PATENT DOCUMENTS

| | | | | |
|---|---|---|---|---|
| JP | 2001299676 A | * | 10/2001 | ............. A61B 1/043 |
| JP | 2004-165728 A | | 6/2004 | |
| JP | 2006-149483 A | | 6/2006 | |
| JP | 2006-187427 A | | 7/2006 | |
| JP | 2006271870 A | * | 10/2006 | ............... A61B 5/11 |
| JP | 2007-075518 A | | 3/2007 | |
| JP | 2009-039561 A | | 2/2009 | |
| JP | 2014-198144 A | | 10/2014 | |
| JP | 2015-012992 A | | 1/2015 | |
| JP | 2016-198369 A | | 12/2016 | |
| WO | WO-2009094465 A1 | * | 7/2009 | ........... A61B 1/0005 |
| WO | 2017/061495 A1 | | 4/2017 | |

* cited by examiner

FIG. 3

| SETTING (PROCEDURE) | COLOR | DETECTION SENSITIVITY | RECORDING METHOD | REPRODUCTION METHOD | REPRODUCTION OUTPUT | OPERATION METHOD | AUTOMATIC LIVE |
|---|---|---|---|---|---|---|---|
| GASTROENTEROLOGICAL SURGERY | GREEN | LOW | MANUAL | NORMAL REPRODUCTION | NORMAL | VIDEO PROCESSOR | OFF |
| OBSTETRICS AND GYNECOLOGY | BLUE | INTERMEDIATE | AUTOMATIC STOP | SLOW REPRODUCTION | PIP | FOOT SWITCH | ON |
| UROLOGICAL SURGERY | WHITE | HIGH | AUTOMATIC RECORDING | LOOP REPRODUCTION | POP | KEYBOARD | |
| .. | .. | .. | | FAST-FORWARD REPRODUCTION | THREE SCREENS | CENTRALIZED CONTROL SYSTEM | |
| | | | | | | .. | |

FIG. 4

| SETTING (PROCEDURE) | COLOR | DETECTION SENSITIVITY | RECORDING METHOD | REPRODUCTION METHOD | REPRODUCTION OUTPUT | OPERATION METHOD |
|---|---|---|---|---|---|---|
| GASTROENTEROLOGICAL SURGERY | — | — | MANUAL | NORMAL REPRODUCTION | NORMAL | PROCESSOR |
| OBSTETRICS AND GYNECOLOGY | — | — | AUTOMATIC STOP | SLOW REPRODUCTION | PIP | FOOT SWITCH |
| UROLOGICAL SURGERY | WHITE | LOW | AUTOMATIC RECORDING | LOOP REPRODUCTION | POP | — |
| ･･ | ･･ | ･･ | ･･ | ･･ | ･･ | ･･ |

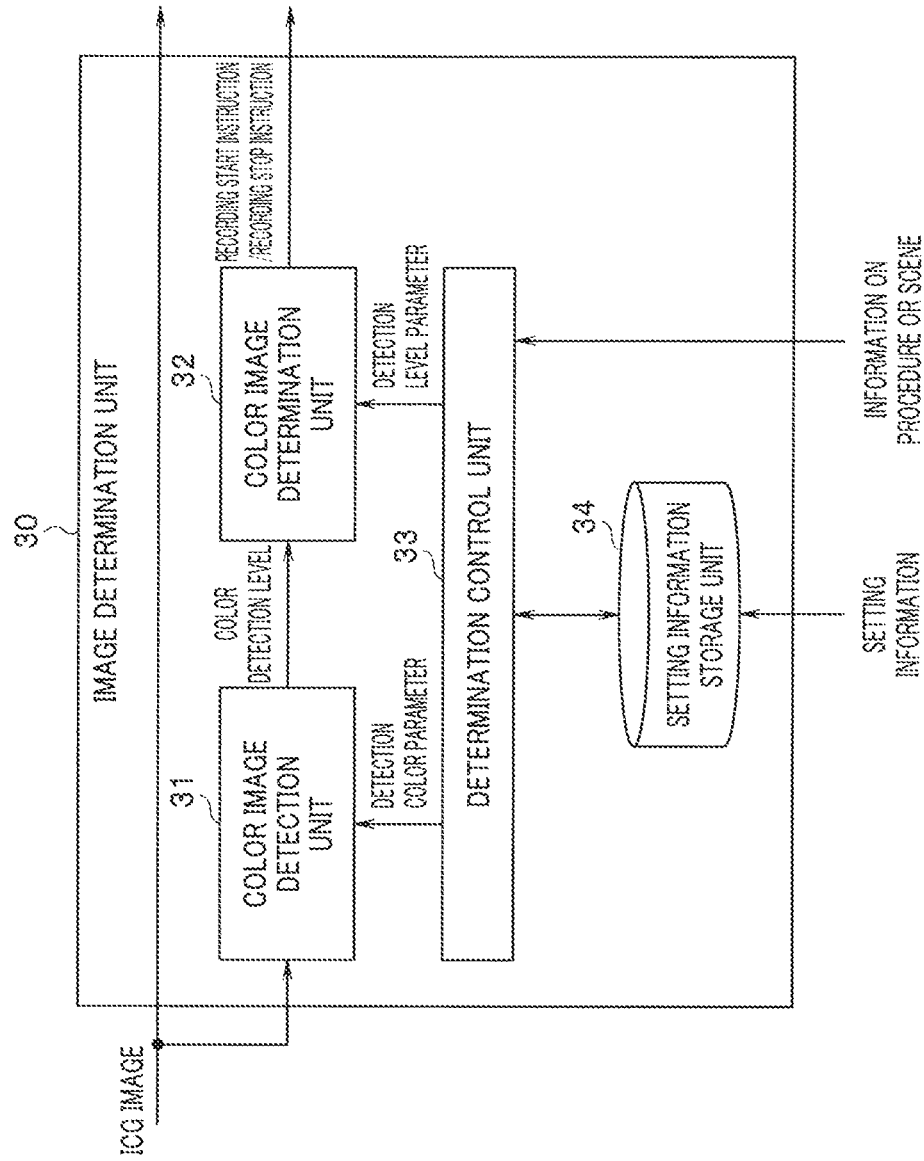

FIG. 9

| SETTING (PROCEDURE) | COLOR | DETECTION SENSITIVITY | RECORDING METHOD | REPRODUCTION METHOD | REPRODUCTION OUTPUT | OPERATION METHOD | AUTOMATIC LIVE |
|---|---|---|---|---|---|---|---|
| GASTROENTEROLOGICAL SURGERY | - | - | MANUAL | NORMAL REPRODUCTION | NORMAL | PROCESSOR | OFF |
| OBSTETRICS AND GYNECOLOGY | - | - | AUTOMATIC STOP | SLOW REPRODUCTION | PIP | FOOT SWITCH | OFF |
| UROLOGICAL SURGERY | WHITE | LOW | AUTOMATIC RECORDING | LOOP REPRODUCTION | THREE SCREENS | - | ON |
| ·· | ·· | ·· | ·· | ·· | ·· | ·· | ·· |

FIG. 12

| SETTING (PROCEDURE) | ICG MODE | | | | ICG REPRODUCTION MODE | | | |
|---|---|---|---|---|---|---|---|---|
| | SW1 | SW2 | SW3 | SW4 | SW1 | SW2 | SW3 | SW4 |
| GASTROENTEROLOGICAL SURGERY | Zoom | Release | ICG Manual REC | ICG PB On | A/B Sel | −1 sec | +1sec | ICG PB Off |
| OBSTETRICS AND GYNECOLOGY | Zoom | Release | ICG Auto REC | ICG PB On | Capture | REW | FF | ICG PB Off |
| UROLOGICAL SURGERY | ICG PB Auto | Release | Zoom | REC | N/A | N/A | N/A | N/A |
| ‥ | ‥ | ‥ | ‥ | ‥ | ‥ | ‥ | ‥ | ‥ |

IMAGE RECORDING APPARATUS, IMAGE RECORDING METHOD, AND ENDOSCOPE SYSTEM

CROSS REFERENCE TO RELATED APPLICATION

This application is a continuation application of PCT/JP2018/045286 filed on Dec. 10, 2018, the entire contents of which are incorporated herein by this reference.

BACKGROUND OF THE INVENTION

1. Field of the Invention

The present invention relates to an image recording apparatus, an image recording method, and an endoscope system each suitable for recording of an image acquired by indocyanine green fluorescence angiography.

2. Description of the Related Art

In a neurosurgical procedure, ICG (indocyanine green) fluorescence angiography is adopted in some cases. The ICG fluorescence angiography is a procedure to observe biological tissues including a blood vessel by capturing, by a medical camera, near-infrared light emitted when ICG combines cd-lipoprotein in the blood.

Some of surgical microscope systems adopted in the neurosurgical procedure include an ICG playback function. The ICG playback function is an important function that is used to support cerebrovascular bypass surgery and the like, and enables check of blood vessel running and bloodstream by recording an ICG observation position and performing loop reproduction.

In recent years, also in endoscopic surgery, for example, in liver surgery or stomach surgery, ICG observation has often been performed for sentinel lymph node identification. Japanese Patent Application Laid-Open Publication No. 2009-39561 proposes a technology about color assignment enabling observation with high contrast in laparoscopic ICG fluorescence navigation surgery.

Further, Japanese Patent Application Laid-Open Publication No. 2014-198144 discloses a surgery support system including a mode in which fluorescence luminance is recorded when the fluorescence luminance becomes higher than or equal to a predetermined value.

SUMMARY OF THE INVENTION

An image recording apparatus according to an aspect of the present invention includes a processor, the processor being configured to record setting information corresponding to at least one of a procedure or a scene during the procedure; set a color to be detected from a fluorescent image and a detection level based on the setting information; detects a level of the set color from the fluorescent image inputted, and outputs signals to start and stop recording of the fluorescent image inputted by comparing the detected level of the color with a threshold based on the detection level.

An image recording method according to another aspect of the present invention, includes: recording setting information corresponding to at least one of a procedure or a scene during the procedure; setting a color to be detected from a fluorescent image and a detection level based on the setting information; detecting a level of the set color from the fluorescent image inputted; and comparing the detected level of the color with a threshold based on the detection level, to thereby determine whether the inputted fluorescent image is usable for identification in an examination, and based on a result of the determination, outputting signals to start and stop recording of the inputted fluorescent image.

An endoscope system according to still another aspect of the present invention, includes: an endoscope; an image pickup control apparatus connected to the endoscope and configured to control image pickup; and an image recording apparatus including a processor, the processor being configured to detect an image signal outputted from the image pickup control apparatus, record setting information corresponding to at least one of a procedure or a scene during the procedure, set a color to be detected from a fluorescent image and a detection level based on the setting information, detect a level of the set color from the fluorescent image inputted, based on a detection result of the image signal, output signals to start and stop recording of the inputted fluorescent image by comparing the detected level of the color with a threshold based on the detection level, and record the fluorescent image during a period when the inputted fluorescent image is determined as being usable for identification, as a result of the comparison.

BRIEF DESCRIPTION OF THE DRAWINGS

FIG. 3 is an explanatory diagram to explain setting information stored in a mode recording/setting unit 26;

FIG. 4 is an explanatory diagram to explain the setting information stored in the mode recording/setting unit 26;

FIG. 5 is a block diagram illustrating an example of a specific configuration of an image determination unit 30 in FIG. 1;

FIG. 9 is an explanatory diagram to explain a second embodiment of the present invention;

FIG. 12 is an explanatory diagram to explain a third embodiment of the present invention.

DETAILED DESCRIPTION OF THE PREFERRED EMBODIMENTS

Embodiments of the present invention are described in detail below with reference to drawings.

First Embodiment

Figure 1:
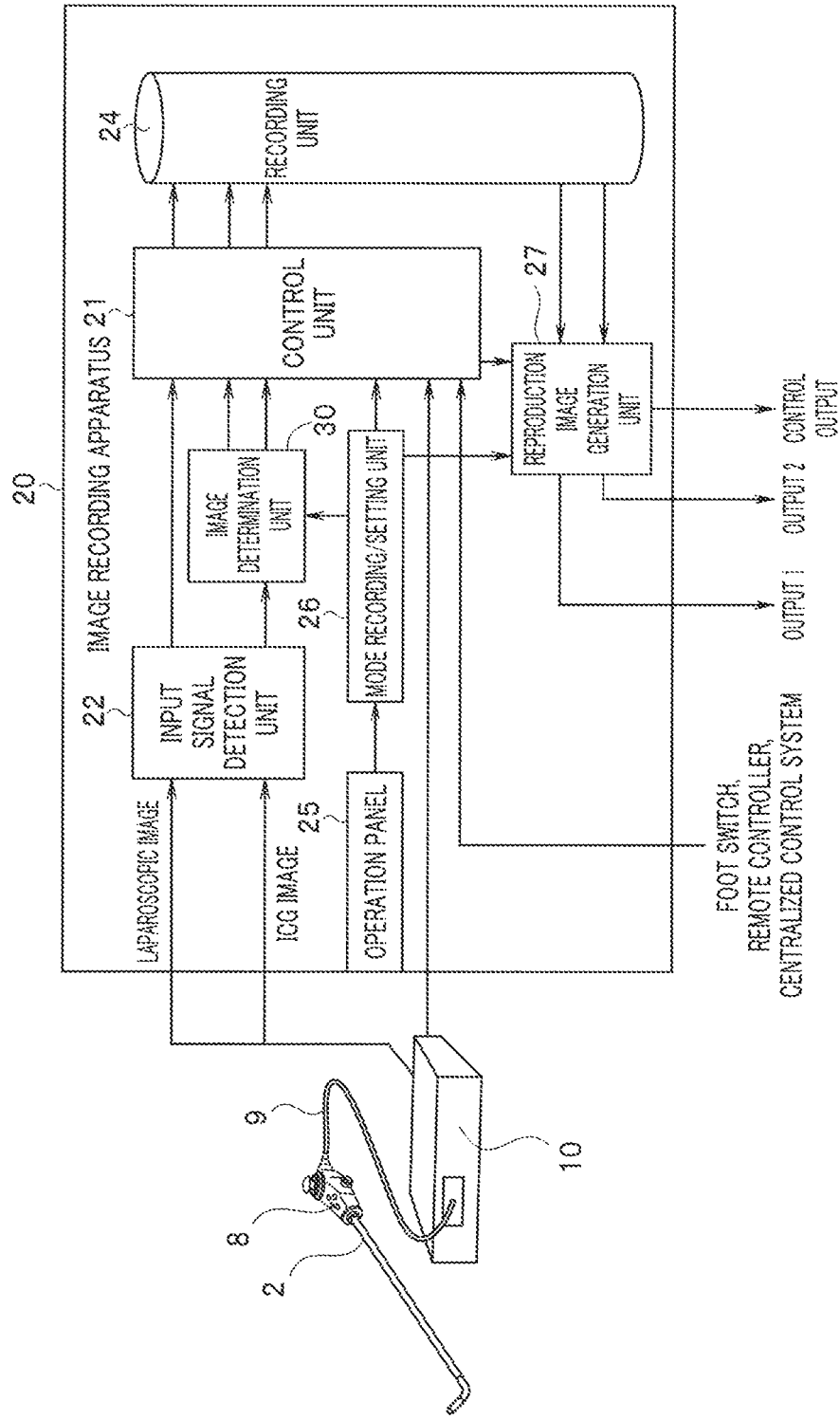
FIG. 1 is a block diagram illustrating an image recording apparatus according to a first embodiment of the present invention.
Figure 2:
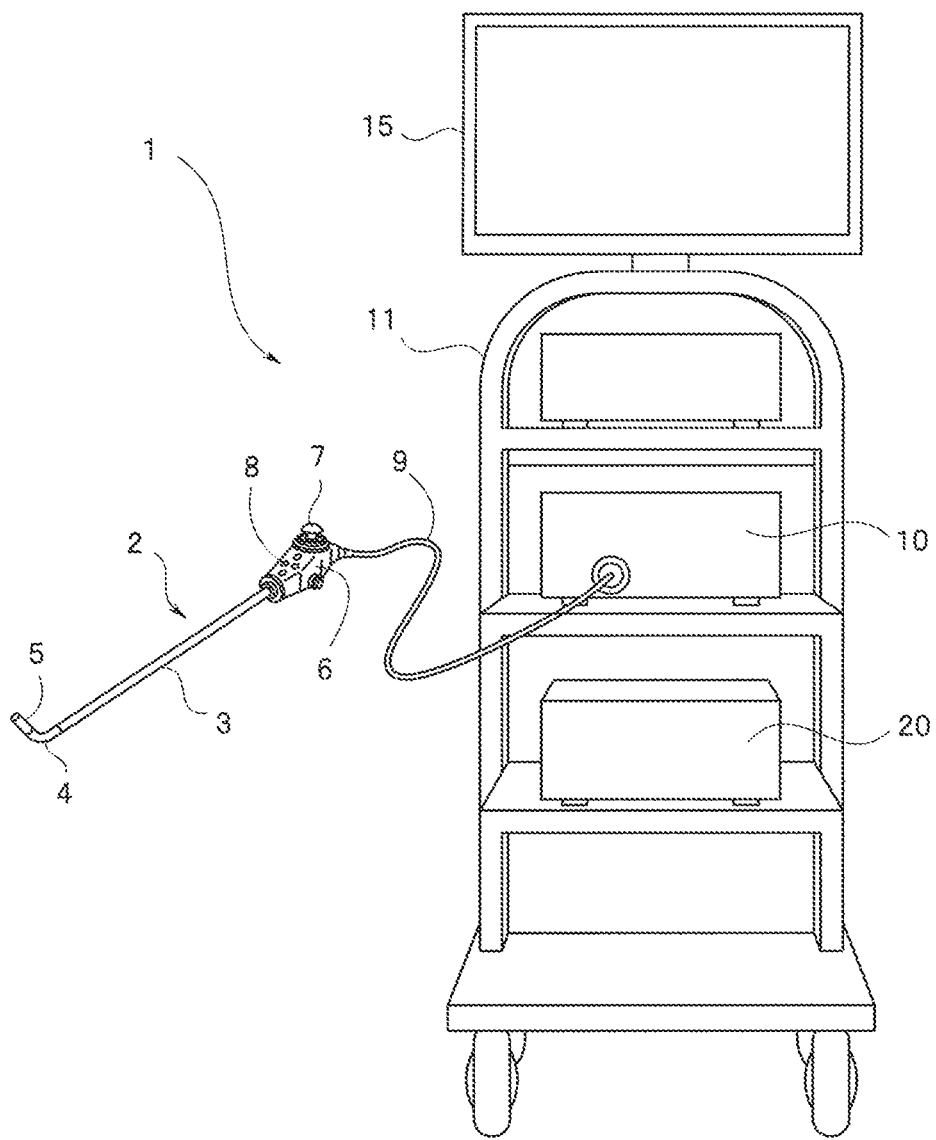
FIG. 2 is an explanatory diagram illustrating an entire configuration of an endoscope system including the image recording apparatus in FIG. 1.

FIG. 1 is a block diagram illustrating an image recording apparatus according to a first embodiment of the present invention. FIG. 2 is an explanatory diagram illustrating an entire configuration of an endoscope system including the image recording apparatus in FIG. 1. The present embodiment adopts determination using color recognition to determine an ICG image and changes color detection accuracy based on a procedure, thereby improving determination accuracy of the ICG image irrespective of a procedure and surely automating recording.

First, the entire configuration of an endoscope system 1 is described with reference to FIG. 2. As illustrated in FIG. 2, the endoscope system 1 includes an endoscope 2, and a camera control unit 10, a monitor 15, and an image recording apparatus 20 placed on a cart 11. The endoscope 2 includes an insertion portion 3 to be inserted into a body. For example, the insertion portion 3 includes a rigid endoscope. The endoscope 2 includes an operation portion 6 on a proximal end side of the insertion portion 3, and includes a bending portion 4 and a distal end portion 5 on a distal end side of the insertion portion 3. The operation portion 6 is provided with a bending lever 7 to bend the bending portion 4 of the insertion portion 3. The operation portion 6 is further provided with a scope switch 8 used for various kinds of operation.

A cable 9 extends from the operation portion 6, and an extending end part of the cable 9 is connected to the camera control unit 10. The camera control unit 10 serving as an image pickup control apparatus includes an unillustrated image processing apparatus (video processor) and a light source apparatus, and controls image pickup by the endoscope 2.

The light source apparatus of the camera control unit 10 can emit white light for normal observation in a normal observation mode, and can emit excitation light (near-infrared light) for ICG observation in an ICG observation mode (fluorescence observation mode). The light from the light source apparatus is transmitted by unillustrated light guides inserted into the cable 9, the operation portion 6, and the insertion portion 3, and is applied as illumination light from the distal end portion 5 to an object.

The distal end portion 5 is provided with an unillustrated image pickup unit. The illumination light reflected by the object enters the image pickup unit provided in the distal end portion 5. The image pickup unit includes an image sensor such as a CCD sensor and a CMOS sensor. The image pickup unit photoelectrically converts the reflected light from the object (object optical image), entering an image pickup surface of the image sensor, to obtain an image pickup signal. In the present embodiment, the image pickup unit can not only pick up an object optical image by normal light but also pick up an object optical image based on fluorescence generated from the ICG by the excitation light applied to the object, under the control of the camera control unit 10.

The image pickup signal from the image pickup unit is supplied to the camera control unit 10 through the cable 9. The video processor inside the camera control unit 10 receives the image pickup signal from the image pickup unit, and performs predetermined signal processing on the received image pickup signal to generate an observation image of the object. The video processor may perform, for example, distortion correction processing, gamma correction processing, emphasis processing, and a white balance correction processing on the observation image. The camera control unit 10 outputs the observation image to the monitor 15 and the image recording apparatus 20. Note that, in the following description, the observation image in the normal observation mode is referred to as a laparoscopic image, and the observation image in the ICG observation mode is referred to as an ICG image or a fluorescent image, in some cases. Note that the observation image obtained in the normal observation mode is not limited to the laparoscopic image.

The monitor 15 includes a liquid crystal panel or the like, and displays the observation image from the camera control unit 10.

In FIG. 1, the image recording apparatus 20 includes a control unit 21, an input signal detection unit 22, an image determination unit 30, a recording unit 24, an operation panel 25, a mode recording/setting unit 26, and a reproduction image generation unit 27. Each of the control unit 21, the image determination unit 30, and the mode recording/setting unit 26 may include a processor using a CPU, an FPGA, or the like, and may operate based on programs stored in an unillustrated memory or realize a part or all of functions by an electric circuit of hardware.

The image recording apparatus 20 includes one or a plurality of unillustrated input terminals. The camera control unit 10 can generate a laparoscopic image and an ICG image as observation images based on the image pickup signal from one endoscope 2, and output the laparoscopic image and the ICG image to the image recording apparatus 20. Further, the camera control unit 10 may receive an image pickup signal from an unillustrated endoscope operating in the normal observation mode and an image pickup signal from an unillustrated endoscope operating in the ICG observation mode at the same timing or at different timings, generate a laparoscopic image and an ICG image based on the image pickup signals at the same timing or at different timings, and output the laparoscopic image and the ICG image to the image recording apparatus 20.

The image recording apparatus 20 may include a plurality of input terminals as an input terminal for a laparoscopic image and an input terminal for an ICG image, and receive a laparoscopic image and an ICG image from the camera control unit 10 at the same timing or at different timings. Further, the image recording apparatus 20 may include one input terminal for both of a laparoscopic image and an ICG image, and receive a laparoscopic image and an ICG image from the camera control unit 10 alternately.

The input signal detection unit 22 detects whether an inputted image is a laparoscopic image or an ICG image. The input signal detection unit 22 provides the laparoscopic image to the control unit 21, and provides the ICG image to the image determination unit 30. Note that the input signal detection unit 22 may detects the laparoscopic image and the ICG image by analyzing an inputted observation image.

The control unit 21 reads out setting information from the mode recording/setting unit 26 serving as a setting unit, and operates based on the setting information. The control unit 21 can generate recording data based on the observation image directly inputted from the input signal detection unit 22 or inputted through the image determination unit 30, and can output the recording data to the recording unit 24. The recording unit 24 includes a predetermined recording medium such as a hard disk device and a memory medium. Recording of the recording unit 24 is controlled by the control unit 21, and the recording unit 24 records an image in a predetermined format.

The reproduction image generation unit 27 serving as an image generation circuit reads out the observation image recorded in the recording unit 24, and generates a reproduction image. The reproduction image generation unit 27 can output the generated reproduction image. FIG. 1 illustrates an example in which the reproduction image generation unit 27 can output two systems. However, the reproduction image generation unit 27 may output one system, or three or more systems. Further, the reproduction image generation unit 27 can also outputs a control output for reproduction control of the outputted reproduction image.

For example, the reproduction image generation unit 27 can switch a monitor as an output destination by the control output. Note that the reproduction image generation unit 27 includes a plurality of operation modes, for example, for switching of an image to be outputted, for switching of a combined output by PIP (picture-in-picture) method/POP (picture-out-picture) method, and for synchronous reproduction of a plurality of recorded observed images.

In the present embodiment, the control unit 21 controls not only recording in response to a command supplied from the camera control unit 10 based on operation of the scope switch 8 of the endoscope 2, but also recording based on the setting of the mode recording/setting unit 26. Further, the image determination unit 30 detects an ICG image (hereinafter, referred to as an identification image) including a portion having characteristics as an ICG image, namely, an image portion enabling identification and diagnosis in various kinds of examinations, from the inputted ICG image, based on the setting information of the mode recording/setting unit 26. In this case, the image determination unit 30 determines the identification image based on the setting information of the mode recording/setting unit 26. Further, the control unit 21 controls the units and controls recording based on the setting of the mode recording/setting unit 26.

FIG. 3 and FIG. 4 are explanatory diagrams to explain the setting information stored in the mode recording/setting unit 26. FIG. 3 illustrates examples of settable items, and FIG. 4 illustrates an example of the setting information stored in the mode recording/setting unit 26.

The operation panel 25 receives operation inputted by a user, and outputs an operation signal to the mode recording/setting unit 26. The mode recording/setting unit 26 generates setting information based on the operation signal, and stores the setting information in an unillustrated internal storage medium and an unillustrated external storage medium.

For example, setting items settable as setting information and information on values set to the setting items may be displayed on an unillustrated display screen of the operation panel 25, and the user may designate setting items and setting values to be registered in the mode recording/setting unit 26 by touching the operation panel 25. Alternatively, as for predetermined setting items, initial values of the setting values previously determined by the system may be registered in the mode recording/setting unit 26. Further alternatively, the user may manually create the setting information and register the created setting information in the mode recording/setting unit 26, or setting information recorded in an unillustrated recording medium may be taken in through a predetermined interface and registered in the mode recording/setting unit 26. Further alternatively, setting information may be read from a server on a network through an unillustrated communication interface.

The user can provide information about a current procedure to the control unit 21 by operating the operation panel 25. Note that the control unit 21 may receive the information about the current procedure from the camera control unit 10 or an unillustrated centralized control system.

The examples of FIG. 3 illustrate that setting (procedure), a color, detection sensitivity, a recording method, a reproduction method, an operation method, and automatic live are settable as the setting items. In the examples of FIG. 3, gastroenterological surgery, obstetrics and gynecology, urological surgery, and so on can be designated as the setting values of the setting item of the setting (procedure). As the color, a green color, a blue color, a white color, and so on can be designated. As the detection sensitivity, low sensitivity, intermediate sensitivity, high sensitivity, and so on can be designated. As the recording method, a manual recording method, an automatic-stop recording method, and an automatic recording method can be designated. As the reproduction method, normal reproduction, slow reproduction, loop reproduction, and fast-forward reproduction can be designated. As the reproduction output, normal output, PIP output, POP output, and three-screen output can be designated. As the operation method, a video processor, a foot switch, a keyboard, and so on can be designated. As the automatic live, off and on can be designated.

In the present embodiment, the color and the detection sensitivity can be registered in the mode recording/setting unit 26 as a condition to detect an identification image as described below, and the color and the detection sensitivity of the setting items are to specify the detection condition.

FIG. 4 illustrates an example of the setting information designated by the user and registered in the mode recording/setting unit 26, among the setting items and the setting values of FIG. 3. In the example of FIG. 4, the manual recording method is designated for the gastroenterological surgery. The recording method of the setting item designates a method of recording the identification image. In a case where the method of recording the identification image is set to the manual recording method, detection of the identification image is not performed. Therefore, the setting values of the color and the detection sensitivity are not set. As operation for recording, the video processor is designated by the setting value of the operation method.

For the obstetrics and gynecology, the automatic-stop recording method is designated. The automatic-stop recording method designates that the recording is automatically ended after a predetermined time determined in the system according to a recording start instruction by the user. In a case where the automatic-stop recording method is adopted, detection of the identification image is not performed. Therefore, the setting values of the color and the detection sensitivity are not set. As operation for recording, the foot switch is designated by the setting value of the operation method.

For the urological surgery, the automatic recording method is designated. In the automatic recording method, the image determination unit 30 determines the identification image, and start and end of the recording are determined based on a determination result. In a case where the automatic recording method is adopted, the color and the detection sensitivity are set for detection of the identification image. In the example of FIG. 4, a white color and low detection sensitivity are adopted. Further, since the recording is automated, the setting value of the operation method is not set.

For example, in a case where the automatic recording method is adopted in the gastroenterological surgery, a green color and intermediate sensitivity are designated for detection of the identification image. Further, for example, in a case where the automatic recording method is adopted in the obstetrics and gynecology, a white color and high detection sensitivity are designated for detection of the identification image.

Note that an example in which, as the method of reproducing the recorded observation image, the normal reproduction is designated for the gastroenterological surgery, the PIP (picture-in-picture) method is adopted in the obstetrics and gynecology, and the POP (picture-out-picture) method is adopted in the urological surgery is illustrated.

Note that the recording method, the color, and the detection sensitivity may be automatically registered in the mode recording/setting unit 26 by the control unit 21 in response to setting of the procedure.

FIG. 5 is a block diagram illustrating an example of a specific configuration of the image determination unit 30 in FIG. 1.

The image determination unit 30 receives the ICG image from the input signal detection unit 22. The image determination unit 30 outputs the inputted ICG image as is to the control unit 21, and also outputs the inputted ICG image to a color image detection unit 31. The image determination unit 30 includes a setting information storage unit 34. Information necessary for detecting the identification image is read out from the mode recording/setting unit 26 and is stored in the setting information storage unit 34. For example, the setting information storage unit 34 stores information about at least the color, the detection sensitivity, and the recording method.

A determination control unit 33 controls the color image detection unit 31 and a color image determination unit 32. The determination control unit 33 receives information [A1] on a procedure or a medical scene based on, for example, operation of the operation panel 25, refers to the setting information storage unit 34 and reads out the setting information based on the information [A1], and generates various kinds of operation parameters to control the color image detection unit 31 and the color image determination unit 32 based on the read setting information. Based on the setting information on color, the determination control unit 33 generates a color parameter (detection color parameter) used for detection of the identification image, and outputs the detection color parameter to the color image detection unit 31. In addition, the determination control unit 33 generates a determination level parameter (detection level parameter) used for detection of the identification image based on detection level setting information, and outputs the detection level parameter to the color image determination unit 32.

The color image detection unit 31 receives designation of the detection color parameter, detects a level of the designated color of the inputted ICG image, and outputs the detected level as numerical value information to the color image determination unit 32. For example, the color image detection unit 31 may output a numerical value that represents the level of the designated color by percentage. Note that the color image detection unit 31 may output an average value of the detection color levels of the whole of the inputted ICG image, or may detect by image analysis an organ to be examined, and output an average value of levels of the organ portion. Further, for example, the determination control unit 33 may provide information on a range designation received from the user, to the color image detection unit 31, and the color image detection unit 31 may output an average value of levels in the designated range.

Note that the color image detection unit 31 may determine, as the above-described average value, an average value for a prescribed period or an average value of a specific range. Further alternatively, the color image detection unit 31 may determine and output a peak value (real time value), in addition to the average value.

The color image determination unit 32 determines whether the inputted level exceeds a threshold based on the detection level designated by the detection level parameter. In a case where the level of the designated color exceeds the threshold, the color image determination unit 32 determines that the inputted ICG image is an image usable for identification (identification image).

In the case where the automatic recording method is designated by the determination control unit 33, the color image determination unit 32 outputs a recording start instruction signal to start recording at a timing when the inputted ICG image is determined as the identification image, and outputs a recording stop instruction signal to stop the recording at a timing when the inputted ICG image is determined as not the identification image.

Figure 6:
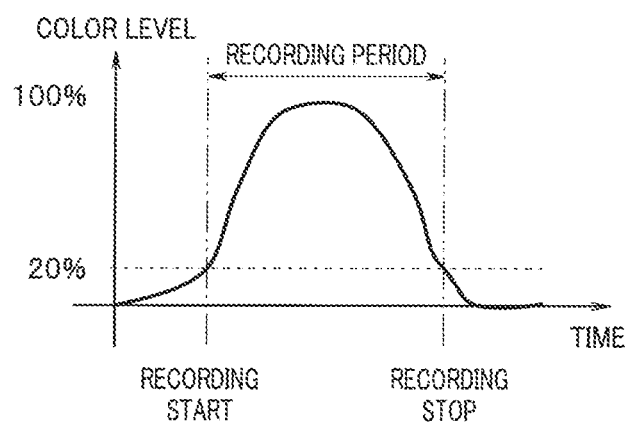
FIG. 6 is a graph to explain a period when an inputted ICG image is determined as an identification image, where a horizontal axis represents time and a vertical axis represents a color level.
Figure 7:
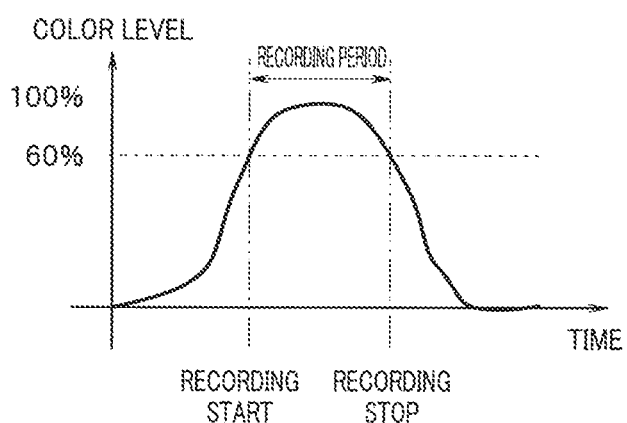
FIG. 7 is a graph to explain the period when the inputted ICG image is determined as the identification image, where a horizontal axis represents the time and a vertical axis represents the color level.

FIG. 6 and FIG. 7 are graphs to explain a period when the inputted ICG image is determined as the identification image, where a horizontal axis represents time and a vertical axis represents a color level. Even in the case of the same procedure, different colors and different detection levels corresponding to various kinds of medical scenes during the procedure may be stored in the setting information storage unit 34. For example, depending on the medical scene, there is a case where it is necessary to check bloodstream of the whole of one organ, and there is a case where it is necessary to check bloodstream of only a reconstructed blood vessel.

For example, in a case where bloodstream of the whole of one organ is checked in the gastroenterological surgery, the color is set to the green color and the detection level is set to 20%, and the image during a period when the level of the green color exceeds the detection level of 20% may be determined as the identification image. FIG. 6 illustrates an example in this case, and the curved line represents the level of the green color outputted from the color image detection unit 31. The image within a range where the level exceeds 20% is determined as the identification image, and the period when the image is determined as the identification image is set as a recording period.

For example, in a case where one reconstructed blood vessel is checked in the gastroenterological surgery, the color is set to the green color and the detection level is set to 60%, and the image during a period when the level of the green color exceeds the detection level of 60% may be determined as the identification image. FIG. 7 illustrates an example in this case, and the curved line represents the level of the green color outputted from the color image detection unit 31. The image within a range where the level exceeds 60% is determined as the identification image, and the period when the image is determined as the identification image is set as a recording period.

The example in which the period when the image is determined as the identification image is set as the recording period has been described. However, hysteresis characteristics may be imparted to start and stop of the recording. For example, the recording may be stopped when the level of the color becomes lower by a predetermined level than the detection level after the recording is started, and the recording may be started when the level of the color becomes higher by a predetermined level than the detection level after the recording is stopped. A pre-recording function in which a movie for the entire period after start of an examination is recorded and a recorded image of the identification image is obtained from the recorded movie from a predetermined period before the period where the image is determined as the identification image, may be provided. Alternatively, a delay stop function in which the recording is stopped after a predetermined time elapses from the end of the period where the image is determined as the identification image, may be provided.

Figure 8:
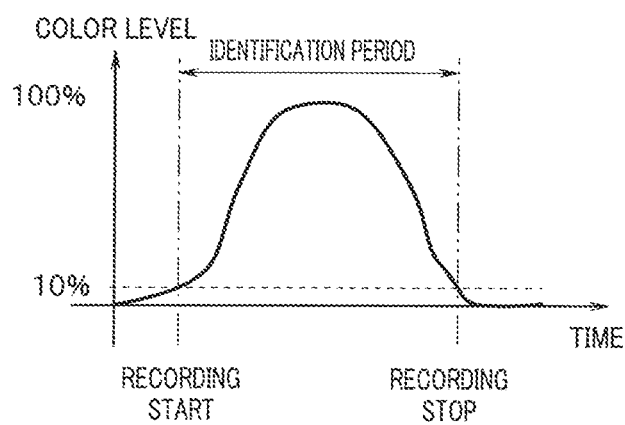
FIG. 8 is a graph to explain the period when the inputted ICG image is determined as the identification image, where a horizontal axis represents the time and a vertical axis represents the color level.

Next, operation of the embodiment configured as described above is described with reference to FIG. 8. FIG. 8 is a graph to explain the period when the inputted ICG image is determined as the identification image, where a horizontal axis represents the time and a vertical axis represents the color level.

The user operates the operation panel 25, and designates and registers the setting information to the mode recording/setting unit 26. It is assumed that the setting information illustrated in FIG. 4 is held in the mode recording/setting unit 26. The setting information storage unit 34 of the image determination unit 30 reads predetermined setting information for determination of the identification image.

The camera control unit 10 supplies the illumination light to the endoscope 2, and controls the image pickup unit to output the image pickup signal. The camera control unit 10 performs the predetermined signal processing on the image pickup signal, acquires the laparoscopic image as the observation image in the normal observation mode, and acquires the ICG image as the observation image in the ICG observation mode. The camera control unit 10 outputs the acquired observation image to the image recording apparatus 20. Note that the camera control unit 10 outputs the laparoscopic image and the ICG image to the image recording apparatus 20 at the same time, in some cases.

The input signal detection unit 22 of the image recording apparatus 20 detects whether the inputted observation image is the laparoscopic image or the ICG image. The input signal detection unit 22 of the image recording apparatus 20 outputs the laparoscopic image to the control unit 21, and outputs the ICG image to the image determination unit 30. When receiving the laparoscopic image, the control unit 21 can generate recording data based on the laparoscopic image, and output the recording data to the recording unit 24. The laparoscopic image is recorded in the recording unit 24 by recording operation of the user in the above-described manner.

It is assumed that observation in the ICG observation mode is performed, and the ICG image is inputted to the image recording apparatus 20. When detecting the ICG image, the input signal detection unit 22 outputs the inputted ICG image to the image determination unit 30. The image determination unit 30 provides the inputted ICG image as is to the control unit 21, and also provides the inputted ICG image to the color image detection unit 31. The determination control unit 33 of the image determination unit 30 reads out the setting information stored in the setting information storage unit 34, sets the detection color parameter to the color image detection unit 31, and sets the detection level parameter to the color image determination unit 32.

It is assumed that the gastroenterological surgery is designated as a procedure. The determination control unit 33 reads out the setting information corresponding to the gastroenterological surgery. As illustrated in FIG. 4, in the case of the gastroenterological surgery, the manual recording method is set, and the determination control unit 33 stops operation of the color image detection unit 31 and the color image determination unit 32.

The control unit 21 also receives a command based on switch operation of the scope switch 8 of the endoscope 2, from the camera control unit 10. In the case of the manual recording method, recording of the ICG image is controlled based on operation of the scope switch 8. In the above-described manner, recording of the ICG image in the recording unit 24 is started at a timing when an operator operates the scope switch 8, and the recording of the ICG image in the recording unit 24 is stopped at a timing when the operator operates the scope switch 8.

It is assumed that the obstetrics and gynecology is designated as a procedure. The determination control unit 33 reads out the setting information corresponding to the obstetrics and gynecology. FIG. 4 illustrates an example in which the automatic-stop recording method is set for the obstetrics and gynecology as an example. In this case, the determination control unit 33 stops operation of the color image detection unit 31 and the color image determination unit 32.

When the operator performs recording start operation by the scope switch 8, a recording start command based on the operation is provided to the control unit 21. In this case, the control unit 21 starts recording of the ICG image in the recording unit 24 in response to the command based on the recording start operation of the scope switch 8. Further, the control unit 21 activates an unillustrated timer when the recording is started, and measures a predetermined time. After the predetermined time elapses, the control unit 21 stops the recording of the ICG image in the recording unit 24. In the case of the automatic-stop recording method, the recording of the ICG image is automatically ended after the predetermined time from the time when the operator performs the recording start operation, in the above-described manner.

It is assumed that the urological surgery is designated as a procedure. The determination control unit 33 reads out the setting information corresponding to the urological surgery. As illustrated in FIG. 4, in the case of the urological surgery, the automatic recording method is set, and the determination control unit 33 sets the parameters based on the setting information to the color image detection unit 31 and the color image determination unit 32.

For example, it is assumed that an image pickup signal acquired in the ICG observation mode is provided from the endoscope 2 to the camera control unit 10, and an image pickup signal acquired in the normal observation mode is provided from an unillustrated other endoscope to the camera control unit 10.

In this case, the camera control unit 10 generates a laparoscopic image and an ICG image. The laparoscopic image and the ICG image are supplied from the input signal detection unit 22 to the control unit 21. In this case, for example, the control unit 21 records the laparoscopic image in the recording unit 24 in response to operation of the scope switch 8 of the endoscope 2, and performs the automatic recording on the ICG image based on the setting in FIG. 4.

The color image detection unit 31 detects a level of a white color of the inputted ICG image, and outputs a detection result to the color image determination unit 32. It is assumed that a level represented by the curved line in FIG. 8 is obtained. It is assumed that, for example, the low detection level parameter of 10% is set to the color image determination unit 32. In this case, when the level of the curved line in FIG. 8 exceeds 10%, the color image determination unit 32 determines that the identification image is inputted, and outputs the recording start instruction signal to the control unit 21. As a result, the control unit 21 starts recording of the inputted ICG image (identification image) in the recording unit 24, irrespective of presence/absence of operation by the operator.

When the level of the curved line in FIG. 8 is lowered to 10% or less, the color image determination unit 32 determines that an image not usable as the identification image is inputted, and outputs a recording stop instruction signal to the control unit 21. As a result, the control unit 21 stops the recording of the inputted ICG image (identification image) in the recording unit 24, irrespective of presence/absence of operation by the operator. In the case of the automatic recording method, the ICG image during the period determined as the input period of the identification image, is automatically recorded in the above-described manner, irrespective of operation by the operator.

In determination of the identification image, the color to be determined and the detection level of the color are set based on the procedure, which makes it possible to significantly improve determination accuracy of the identification image. As a result, it is possible to surely and automatically record the identification image enabling identification in the examination, irrespective of the procedure.

As described above, in the present embodiment, the ICG image is determined using color recognition, which makes it possible to improve determination accuracy. In addition, the color and the color detection level are changed based on the procedure and the scene, which makes it possible to improve determination accuracy of the ICG image irrespective of the procedure and the scene, and to surely and automatically record the identification image enabling identification in the examination.

Note that, as the automatic recording method, the example in which start and end of recording are automated by determination of the identification image has been described, but at least one of start or end of the recording may be automated.

In the present embodiment, the identification image is recorded during the period (identification period) when the inputted ICG image is determined as the identification image. However, the recording may be started at a timing before and after a predetermined period from the start timing of the identification period, and the recording may be ended at a timing before and after a predetermined period from the end timing of the identification period.

Second Embodiment

Figure 10:
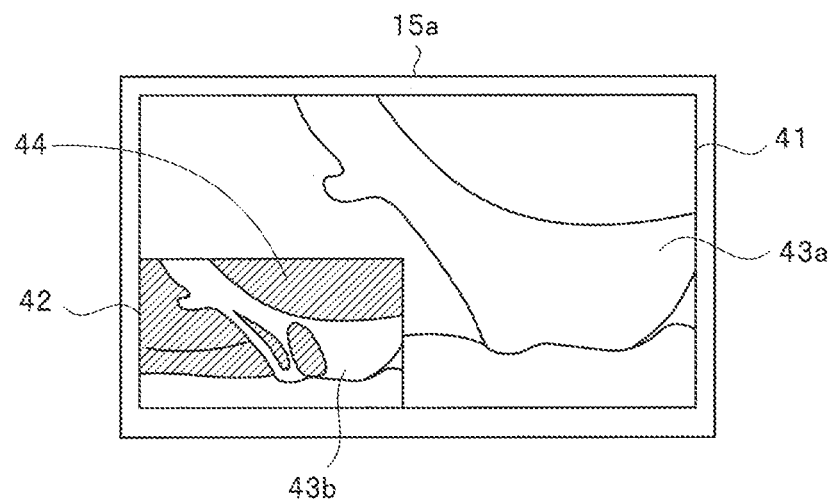
FIG. 10 is an explanatory diagram to explain the second embodiment of the present invention.
Figure 11:
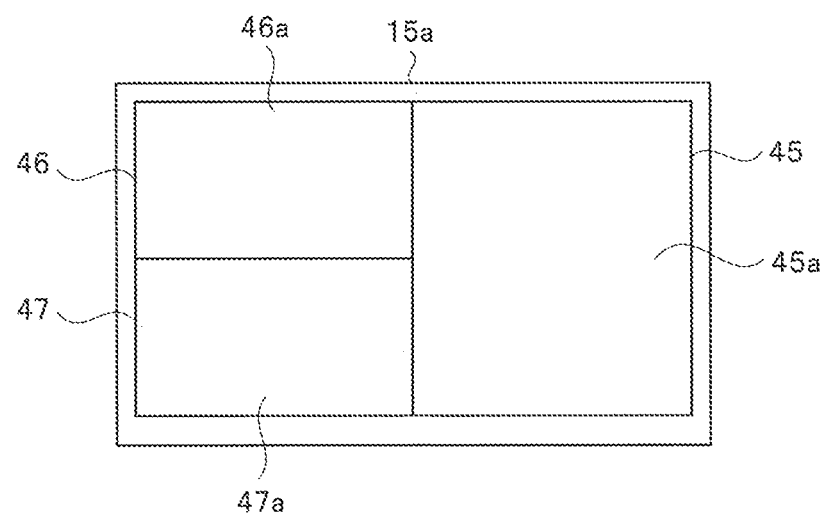
FIG. 11 is an explanatory diagram to explain the second embodiment of the present invention.

FIG. 9 to FIG. 11 are explanatory diagrams to explain a second embodiment of the present invention. A hardware configuration of the present embodiment is similar to the hardware configuration of the first embodiment. In the present embodiment, a specific example in reproduction is described.

FIG. 9 illustrates an example of the setting information recorded in the mode recording/setting unit 26. The control unit 21 controls an operation mode of the reproduction image generation unit 27 based on the user operation and the setting information in the mode recording/setting unit 26. The reproduction image generation unit 27 generates a reproduction image based on control by the control unit 21 and the setting information in the mode recording/setting unit 26. For example, the control unit 21 outputs a command to the reproduction image generation unit 27 in response to reproduction start operation and reproduction stop operation by the operator. In this case, the reproduction image generation unit 27 reads out the observation image recorded in the recording unit 24 and generates a reproduction image under the control of the control unit 21.

The operation mode of the reproduction image generation unit 27 may be designated to an operation mode based on the setting information in the mode recording/setting unit 26, by the control unit 21. For example, in a case where the loop reproduction is designated by the setting information, when receiving reproduction start instruction from the control unit 21, the reproduction image generation unit 27 repeatedly reproduces the reproduction image generated based on the observation image recorded in the recording unit 24.

FIG. 9 illustrates an example in which the reproduction method is designated for each of the procedures. In the example of FIG. 9, normal screen output by normal reproduction is designated for the gastroenterological surgery. According to the designation, the reproduction image generation unit 27 reads out the observation image recorded in the recording unit 24, and reproduces the observation image at normal speed. The reproduction image from the reproduction image generation unit 27 is supplied to the monitor 15 or the like, and is displayed on a display screen.

Further, in the example of FIG. 9, PIP screen output by slow reproduction is designated for the obstetrics and gynecology. According to the designation, the reproduction image generation unit 27 reads out the observation image recorded in the recording unit 24. In this case, the PIP screen is designated, and a reproduction image to be displayed on primary and secondary screens is generated. For example, it is assumed that observation in the normal observation mode and observation in the ICG observation mode are performed at the same time, and a laparoscopic image and an ICG image are acquired at the same time and are recorded in the recording unit 24. In this case, the reproduction image generation unit 27 generates the reproduction image by the PIP method in which, for example, the laparoscopic image is handled as a primary image and the ICG image is handled as a secondary image during the recording period designated by the operator, and slowly reproduces the reproduction image.

FIG. 10 illustrates an example of the reproduction image reproduced and displayed on a display screen 15*a* of the monitor 15 in this case. In the example of FIG. 10, the display screen 15*a* includes a primary screen 41 and a secondary screen 42, a laparoscopic image 43*a* is displayed as a primary image on the primary screen 41, and an ICG image 43*b* is displayed as a secondary image on the secondary screen 42. The ICG image 43*b* is displayed in a display format that enables a fluorescent portion 44 (hatched portion) usable for identification in the examination, to be clearly visually recognized. Although the fluorescent portion 44 is changed with time, slow reproduction facilitates check of the fluorescent portion 44.

In the example of FIG. 9, three-screen output by loop reproduction is designated for the obstetrics and gynecology. According to the designation, the reproduction image generation unit 27 reads out the observation image recorded in the recording unit 24. In this case, three-screen output is designated, and the reproduction image for three-screen display is generated. For example, it is assumed that observation in the normal observation mode and observation in the ICG observation mode are performed at the same time, and a laparoscopic image and an ICG image are acquired at the same time and are recorded in the recording unit 24. Further, it is assumed that an observation image being currently acquired is provided from the control unit 21 to the reproduction image generation unit 27.

In this case, the reproduction image generation unit 27 generates the reproduction image by the three-screen method in which, for example, the current observation image is handled as a first image, the laparoscopic image is handled as a second image, and the ICG image is handled as a third image. Note that the laparoscopic image and the ICG image read out from the recording unit 24 and generated are continuously loop-reproduced during the recording period based on operation by the operator. The screen configuration and the target of the loop reproduction are appropriately changeable.

FIG. 11 illustrates an example of the reproduction image reproduced and displayed on the display screen 15a of the monitor 15 in this case. In the example of FIG. 11, the display screen 15a includes a first screen 45, a second screen 46, and a third screen 47. A current observation image 45a is displayed on the first screen 45, a laparoscopic image 46a for a predetermined recording period is loop-reproduced and displayed on the second screen 46, and an ICG image 47a for the predetermined recording period is loop-reproduced and displayed on the third screen 47. As a result, the operator can check the laparoscopic image 46a and the ICG image 47a for the recording period necessary for identification in the examination while checking the current observation image, which facilitates identification in the examination.

As described above, in the present embodiment, the recorded observation image can be reproduced by an optional reproduction method and an optional screen configuration, which facilitates identification in the examination. Further, since the reproduction method and the screen configuration corresponding to the procedure are automatically set based on the setting information, a complicated setting work is unnecessary, and it is possible to check the image by the optimum reproduction method and the optimum screen configuration corresponding to the procedure.

Third Embodiment

FIG. 12 is an explanatory diagram to explain a third embodiment of the present invention. A hardware configuration of the present embodiment is similar to the hardware configuration of the first embodiment. The present embodiment is to improve operability for recording reproduction of the ICG image.

FIG. 12 illustrates an example of the setting information recorded in the mode recording/setting unit 26. The setting information in FIG. 12 is to control operation by the scope switch 8 of the endoscope 2 operating in the ICG observation mode. FIG. 12 illustrates an example in which the scope switch 8 includes four switches SW1 to SW4.

The switches SW1 to SW4 of the scope switch 8 are assigned to predetermined commands in the normal observation mode. When any of these switches SW1 to SW4 is operated, the camera control unit 10 supplies the command assigned to the operated switch, to the control unit 21 of the image recording apparatus 20.

When any of the switches SW1 to SW4 is operated in the ICG observation mode, the camera control unit 10 supplies information to identify each of the switches SW1 to SW4, for example, a switch number, to the control unit 21 of the image recording apparatus 20, in place of the commands assigned to these switches. Further, in a case where the endoscope 2 is driven in the ICG observation mode, the camera control unit 10 transmits information representing the ICG observation mode, to the control unit 21 of the image recording apparatus 20.

Note that in a case where two endoscopes that are an endoscope operating in the normal observation mode and an endoscope operating in the ICG observation mode are connected, the camera control unit 10 transmits the assigned command to the image recording apparatus 20 when the scope switch of the endoscope operating in the normal observation mode is operated, and transmits the switch number to the image recording apparatus 20 when the scope switch of the endoscope operating in the ICG observation mode is operated.

Setting in an ICG mode in FIG. 12 is operation setting in the normal ICG observation by the endoscope 2, and setting in an ICG reproduction mode is operation setting in reproduction of the recorded ICG image. As illustrated in FIG. 12, in the present embodiment, the operations assigned to the switches SW1 to SW4 are different depending on the procedure.

In the ICG mode, in the case of the gastroenterological surgery, for example, zoom (Zoom), release (Release), manual recording (ICG Manual REC), and reproduction mode start (ICG PB On) are respectively assigned to the switches SW1 to SW4. In the case of the obstetrics and gynecology, zoom, release, automatic recording (ICG Auto REC), and reproduction mode start (ICG PB On) are respectively assigned to the switches SW1 to SW4. In the case of the urological surgery, automatic reproduction (ICG PB Auto), release, zoom, and recording (REC) are respectively assigned to the switches SW1 to SW4.

In the ICG reproduction mode, in the case of the gastroenterological surgery, for example, A/B selection (A/B Sel), one second before (−1 sec), one second after (+1 sec), and reproduction mode end (ICG PB Off) are respectively assigned to the switches SW1 to SW4. In the case of the obstetrics and gynecology, capture (Capture), rewind (REW), fast-forward (FF), and reproduction mode end (ICG PB Off) are respectively assigned to the switches SW1 to SW4. Note that in the case of the urological surgery, no operation is assigned to the switches SW1 to SW4 (N/A).

Next, operation of the embodiment configured as described above is described.

For example, the user operates the operation panel 25, and registers the setting information in the mode recording/setting unit 26. It is assumed that the endoscope 2 operates in the ICG observation mode. In this case, the camera control unit 10 transmits information representing the ICG observation mode, to the control unit 21 of the image recording apparatus 20. Further, when any of the switches of the scope switch 8 is operated, the camera control unit 10 transmits the switch number of the operated switch to the control unit 21.

In a case where the ICG observation mode is designated from the camera control unit 10, the control unit 21 receives the information on the switch number based on the operation of the scope switch 8, and refers to the setting information in the mode recording/setting unit 26 by using the switch number, thereby performing operation designated by the setting information.

Further, the control unit 21 receives information about a current procedure from the camera control unit 10, the unillustrated centralized control system, or the like. Alternatively, the user operates the operation panel 25 to input the information about the current procedure. As a result, the control unit 21 recognizes that the current procedure is, for example, the gastroenterological surgery, the obstetrics and gynecology, or the urological surgery.

It is assumed that the ICG observation by the endoscope 2 is performed in the gastroenterological surgery, and the endoscope 2 operates in the ICG mode in FIG. 12. In this case, for example, when the switch SW3 of the scope switch 8 is operated, the control unit 21 determines that the manual recording operation has been performed, and provides the inputted observation image to the recording unit 24 to start recording. When the switch SW3 of the scope switch 8 is operated while the observation image is recorded, the control unit 21 determines that operation to end the manual recording has been performed, and stops the recording of the observation image.

It is assumed that the ICG observation by the endoscope 2 is performed in the obstetrics and gynecology. In this case, when the switch SW3 of the scope switch 8 is operated, the control unit 21 determines that the automatic recording has been designated. In this case, the information on the period when the identification image is detected by the determination of the image determination unit 30 is supplied to the control unit 21, and the control unit 21 records the ICG image in the recording unit 24 during the period when the identification image is detected, based on the information from the image determination unit 30. Note that when the recording start time point is denoted by A and the recording end time point is denoted by B, the observation image during the period from A to B is recorded.

When the switch SW3 is operated in the urological surgery or when the switch SW1 is operated in the gastroenterological surgery or the obstetrics and gynecology, the control unit 21 determines that the zoom operation has been performed, and performs enlargement or reduction processing of the observation image. When the switch SW2 is operated, the control unit 21 determines that the release operation has been performed, and records a still image of the inputted observation image in the recording unit 24.

When the switch SW4 is operated in the ICG observation in the gastroenterological surgery or the obstetrics and gynecology, the control unit 21 switches the mode between the ICG mode and the ICG reproduction mode. More specifically, when the switch SW4 is operated in the ICG mode, the mode is transited to the ICG reproduction mode, whereas when the switch SW4 is operated in the ICG reproduction mode, the mode is transited to the ICG mode. When the ICG reproduction mode is designated by the switch SW4, the control unit 21 instructs the reproduction image generation unit 27 to reproduce the observation image recorded in the recording unit 24. The reproduction image generation unit 27 reads out the observation image from the recording unit 24 to generate the reproduction image, and outputs the generated reproduction image to the monitor 15. As a result, the observation image can be reproduced and displayed on the display screen of the monitor 15.

When the switch SW1 is operated in the ICG reproduction mode in the gastroenterological surgery, the control unit 21 alternately switches and selects the start time point A and the end time point B for each operation. Further, when the switch SW2 is operated, the start time point A or the end time point B is moved forward by one second for each operation. When the switch SW3 is operated, the start time point A or the end time point B is moved backward by one second for each operation. Note that the number of seconds moved for each operation is not limited to one, but is optionally settable.

Note that the movement of the time by the operation of the switches SW2 and SW3 is possible only within the period from A to B. Further, for example, in a case where the recording for a period longer than the period from A to B by the operation of the switch SW3 in the ICG mode is performed by using, for example, an unillustrated buffer, the operation of the switches SW2 and SE3 is validated within the recording range.

When the switch SW1 is operated during reproduction of the ICG movie in the ICG reproduction mode in the obstetrics and gynecology, the image at the operation timing is captured and is recorded in the recording unit 24. Further, when the switch SW2 is operated, reproduction position is rewound. When the switch SW3 is operated, the reproduction position is fast-forwarded.

When the switch SW2 is operated in the ICG mode in the urological surgery, the control unit 21 determines that the release operation has been performed. When the switch SW3 is operated, the control unit 21 determines that the zoom operation has been performed. When the switch SW4 is operated, the control unit 21 determines that the recording start operation or the recording end operation has been performed.

In the ICG mode in the urological surgery, a function that automatically performs reproduction is assigned to the switch SW1. For example, when the switch SW1 is continuously depressed for a predetermined time or more (hereinafter, referred to as long depression), the control unit 21 performs control to start the recording at that timing and to stop the recording after a preset predetermined time. Further, after the recording is stopped, the control unit 21 automatically reproduces the image for the recording period. Note that when the switch SW1 is continuously depressed for a predetermined time or less (hereinafter, referred to as short depression) during the reproduction, the control unit 21 returns a reproduction position to a head position of the recording. When the switch SW1 is short-depressed at time other than the reproduction, the control unit 21 performs reproduction from the head position of the recording again. Note that overwrite recording is performed in response to the long depression of the switch SW1. Setting of such operation is appropriately changeable, and for example, the recording may be started in response to short depression and the reproduction may be performed in response to long depression.

In the above-described embodiment, description has been made on the example using the setting information in which the switches of the scope switch are assigned to the respective operations. When assignment of the various kinds of operation devices such as the keyboard and the foot switch to the operation is described in the setting information, it is possible to control the recording reproduction operation and other operation of the ICG image by using not only the scope switch but also the various kinds of operation devices such as the keyboard and the foot switch.

As described above, in the present embodiment, for example, the setting information representing assignment of the switches of the scope switch to the operation is used, the information identifying each of the switches of the scope switch is transmitted in place of the command assigned to the scope switch, and the recording reproduction operation of the ICG image is controlled by referring to the setting information based on the information identifying each of the switches. This makes it possible to easily perform recording and reproduction of the ICG image. In addition, different settings corresponding to the procedure and the scene may be set in the setting information, and desired operability corresponding to the procedure and the scene can be obtained. Further, the operation can be performed through an apparatus such as the scope switch, disposed in a sterilized area, which can eliminate previous drape operation.

Further, the function to switch the mode between the ICG mode used for recording of the ICG image and the ICG reproduction mode used for reproduction of the ICG image is assigned to one of the switches of the scope switch. This makes it possible to assign a relatively large number of functions to a small number of switches. For example, recording and reproduction of the ICG image can be instructed by operation of the scope switch, the keyboard, the foot switch, and the like. In addition, in the reproduction, operation of these switches can perform stop, reproduction, pause, and a plurality of reproduction modes such as loop reproduction, slow reproduction, reverse reproduction, fast-reverse reproduction, and fast-forward reproduction. Furthermore, playback reproduction can be automatically performed after the recording is stopped.

The functions of the mode recording/setting unit 26, the image determination unit 30, and the control unit 21 according to the above-described embodiments may be provided in the camera control unit 10 or the video processor inside the camera control unit 10. In this case, the camera control unit 10 causes the switches of the scope switch 8 to output the respective commands assigned based on the setting information. Accordingly, in this case, a common recording apparatus can be adopted as the recording apparatus.

Note that, in the embodiments, a portion described as a "unit" may be configured by a dedicated circuit or by combining a plurality of general-purpose circuits, and may be configured by combining a microcomputer performing based on previously programmed software, a processor such as a CPU, and a sequencer such as an FPGA, as necessary.

The present invention is not limited to the above-described embodiments, and can be embodied by modifying the components without departing from the gist of the present invention in implementation. Further, various inventions can be made by appropriate combinations of the plurality of components disclosed in the above-described embodiments. For example, some of the components described in the embodiments may be deleted. Further, the components of the different embodiments may be appropriately combined.

What is claimed is:

1. An image recording apparatus comprising:
a processor comprising hardware, and
an image generation circuit configured to perform a reproduction operation based on control by the processor and setting information,
wherein the processor being configured to:
record setting information corresponding to at least one of a procedure or a scene during the procedure;
set a color to be detected from a fluorescent image and a detection level based on the setting information;
detect a level of the set color from the fluorescent image inputted; and
output signals to start and stop recording of the inputted fluorescent image by comparing the detected level of the color with a threshold based on the detection level, and record an observation image acquired in a normal observation mode and the fluorescent image acquired in a fluorescence observation mode at a same time, and
wherein the image generation circuit generates a reproduction image to display the observation image acquired in the normal observation mode and the fluorescent image at the same time.

2. The image recording apparatus according to claim 1, wherein the processor sets the setting information based on user operation, or sets the setting information to an initial value based on at least one of the procedure or the scene during the procedure.

3. The image recording apparatus according to claim 2, wherein the processor sets each of the color and the detection level to an initial value corresponding to at least one of the procedure or the scene during the procedure.

4. The image recording apparatus according to claim 1, wherein, in a case where automatic recording is designated by the setting information, the processor sets the color to be detected from the fluorescent image and the detection level.

5. The image recording apparatus according to claim 1, wherein the processor changes setting of the color and the detection level depending on the scene during the procedure even in the same procedure.

6. The image recording apparatus according to claim 1, wherein
the processor performs control to record the fluorescent image during a period when the inputted fluorescent image is determined as being usable for identification in an examination,
the processor can record an observation image acquired in a normal observation mode and the fluorescent image acquired in a fluorescence observation mode at a same time,
the processor controls start and end of recording of the observation image acquired in the normal observation mode, based on user operation, and
the processor controls start and end of recording of the fluorescent image, based on a comparison result between the detected level of the color and a threshold based on the detection level.

7. The image recording apparatus according to claim 1, wherein
the processor performs control to record the fluorescent image during a period when the inputted fluorescent image is determined as being usable for identification in an examination, as a result of the comparison.

8. An image recording apparatus comprising:
an image generation circuit; and
a processor comprising hardware, the processor being configured to:
record setting information corresponding to at least one of a procedure or a scene during the procedure;
set a color to be detected from a fluorescent image and a detection level based on the setting information;
detect a level of the set color from the fluorescent image inputted; and
output signals to start and stop recording of the inputted fluorescent image by comparing the detected level of the color with a threshold based on the detection level,
wherein the image generation circuit being configured to generate a reproduction image based on the recorded fluorescent image,
the processor performs control to record the fluorescent image during a period when the inputted fluorescent image is determined as being usable for identification in an examination, as a result of the comparison,
the image generation circuit performs reproduction operation based on control by the processor and the setting information,
the processor can record an observation image acquired in a normal observation mode and the fluorescent image acquired in a fluorescence observation mode at a same time, and
the image generation circuit generates a reproduction image to display the observation image acquired in the normal observation mode and the fluorescent image at the same time by a picture-in-picture method or a picture-out-picture method.

9. An image recording method, comprising:
recording setting information corresponding to at least one of a procedure or a scene during the procedure;
setting a color to be detected from a fluorescent image and a detection level based on the setting information;

detecting a level of the set color from the fluorescent image inputted; and comparing the detected level of the color with a threshold based on the detection level, to thereby determine whether the inputted fluorescent image is usable for identification in an examination, and based on a result of the determination, outputting signals to start and stop recording of the inputted fluorescent image.

10. An endoscope system, comprising:

an endoscope;

an image pickup control apparatus connected to the endoscope and configured to control image pickup; and an image recording apparatus including a processor comprising hardware, the processor being configured to:
- detect an image signal outputted from the image pickup control apparatus;
- record setting information corresponding to at least one of a procedure or a scene during the procedure;
- set a color to be detected from a fluorescent image and a detection level based on the setting information;
- detect a level of the set color from the fluorescent image inputted, based on a detection result of the image signal;
- output signals to start and stop recording of the inputted fluorescent image by comparing the detected level of the color with a threshold based on the detection level, and
- record the fluorescent image during a period when the inputted fluorescent image is determined as being usable for identification, as a result of the comparison.

* * * * *